(12) United States Patent
Konopa et al.

(10) Patent No.: US 6,589,961 B2
(45) Date of Patent: Jul. 8, 2003

(54) 9-ALKYLAMINO-1-NITROACRIDINE DERIVATIVES

(75) Inventors: Jerzy Kazimierz Konopa, Gdansk (PL); Barbara Wysocka-Skrzela, Gdansk (PL); Raj Tiwari, Bellrose, NY (US)

(73) Assignee: New York Medical College, Valhalla, NY (US)

( * ) Notice: Subject to any disclaimer, the term of this patent is extended or adjusted under 35 U.S.C. 154(b) by 0 days.

(21) Appl. No.: 09/934,715

(22) Filed: Aug. 22, 2001

(65) Prior Publication Data

US 2002/0099211 A1 Jul. 25, 2002

Related U.S. Application Data

(63) Continuation-in-part of application No. 09/788,056, filed on Feb. 16, 2001, now abandoned.
(60) Provisional application No. 60/183,530, filed on Feb. 18, 2000.

(51) Int. Cl.$^7$ .................. A61K 31/473; C07D 219/10; C07D 219/06; A61P 35/00; A61P 35/04
(52) U.S. Cl. ....................................... 514/297; 546/105
(58) Field of Search ........................... 514/297; 546/105

(56) References Cited

U.S. PATENT DOCUMENTS

| 4,139,531 A | 2/1979 | Ledóchowski et al. ..... 546/106 |
| 4,150,231 A | 4/1979 | Ledóchowski et al. ..... 546/106 |
| 5,814,602 A | 9/1998 | Steck .......................... 260/279 |

FOREIGN PATENT DOCUMENTS

EP          038 572      10/1980

OTHER PUBLICATIONS

Bundgaard H. Designs of Prodrugs. (1985). Elsevier. pp. 1–3.*
Lee et al., 1996, J. Med. Chem. 39:2508–251.
Robertson et al., 1996, Xenobiotica 26:559–569.
Gniazdowsk et al., 1995, Gen. Pharmacol. 26:473–480.
Monge, A. et al., 1994, J. Heterocyclic Chem. 31:1455–1460.
Cholody, et al., 1991, J. Heterocyclic Chem. 28: 209–214.
Denny et al. 1990, J. Med. Chem. 33:1288–1295.
Mazerska et al., 1990, Anti–Cancer Drug Des. 5:169–187.
Wilson et al., 1989, J. Med Chem. 32:23–30.
Ferguson et al. 1987, *Mutagenesis* 2: 253–256.
Mazerska et al., 1984, Eur. J. Med. Chem. 19:199–204.
Pawlak et al., 1984, Cancer Res. 44:4829–4296.
Cholody et al., 1983, Pol. J. Chem. 57:285–290.
Hrabowska et al., 1982 Arzneimittel–Forschung 32:1013–6.
Gniazdowski et al., 1982, Cancer Letters 15:73–79.
Joseph et al., 1996, Proc. Natl. Acad. Sci. U.S.A. 93:8552–8557.
Wysocka–Skrzela et al., 1981, Pol. J. Chem. 55:2211–2214.
Sofina et al., 1980, Experimental Evaluation of Antitumor Drugs in the USA and USSR and Clinical Correlations. NIH Publication No. 80–1933.
Wysocka–Skrzela et al., 1980, Pol. J. Chem. 54:619–623.
Ledochowski, 1976, Mat. Med. Pol. 8:1–15.
Kolodziejczyk et al., 1975, J. Labelled Compounds 11:385–394.
Cain et al., 1974, J. Med. Chem. 173:922–930.
Horowska et al., 1968, Roczniki Chemii, Ann. Soc. Chim. Polonorum 42:1351–5.
Steck, E.A. et al., 1957, J. Am. Chem. Soc. 79:4414–4417.
Yekundi, et al., 1957, *Chem. Ber.* 90:2448–2450.

\* cited by examiner

*Primary Examiner*—Evelyn Mei Huang
(74) *Attorney, Agent, or Firm*—Cheryl H. Agris

(57) ABSTRACT

The invention is directed to novel 9-hydroxyalkylamino-, 9-alkoxyalkylamino-1-nitroacridine derivatives. Methods of preparation, pharmaceutical compositions comprising said derivatives and their medical uses are also encompassed by this invention.

23 Claims, 2 Drawing Sheets

9-ALKYLAMINO-1-NITROACRIDINE DERIVATIVES

PRIORITY CLAIM

This application claims priority from provisional application Ser. No. 60/183,530, filed Feb. 18, 2000, under 35 U.S.C. §119(e), the contents of which are incorporated herein by reference and is a continuation-in-part of application serial no. 09/788,056, filed Feb. 16, 2001 abandoned, the contents of which are incorporated herein by reference.

FIELD OF THE INVENTION

The invention is directed to novel 9-hydroxyalkylamino- and 9-alkoxyalkylamino-1-nitroacridine derivatives. Methods of preparation, compositions comprising said derivatives and their medical uses are also encompassed by this invention.

BACKGROUND OF THE INVENTION

Acridines are potent biological molecules that bind to DNA and inhibit cell growth. A number of derivatives of acridine have been studied for antitumor activity. Earlier work showed that 1-nitro-9-alkylaminoalkylaminoacridines had good antitumor activity (see, for example, U.S. Pat. No. 4,139,531, Gniazdowsk et al., 1995, Gen. Pharmacol. 26:473, Ledochowski, 1976, Mat. Med. Pol. 3:237, Mazerska et al., 1984, Eur. J. Med. Chem. 19:199, Pawlak et al., 1984, Cancer Res. 44:4289, Mazerska et al., 1990, Anti-Cancer Drug Des. 5:169, Hrabowska et al., 1982, Arzneim-Forsch./Drug. Res. 32:1013–1016). It has been found that introduction of a hydroxyalkyl amino group into position 9 of 1-nitroacridine, also provides active compounds (EP 38572).

Despite a large body of data on derivatives of acridines (Mazerska, Z. et al., 1984 Eur. J. Med. Chem. 19: 1999; Mazerska, Z. et al., 1990, Anticancer Drug Des. 5:169), the introduction of new substituents into the system still can provide unexpected results. As an illustration, studies on mutagenicity of various derivatives of nitracrine demonstrated different characteristics for individual compounds (Ferguson et al. 1987, *Mutagenesis* 2:253). It was also found that the introduction of 4-methoxy substituent into nitracrine moiety decreased the overall metabolism in comparison with the unsubstituted compound in rat (Robertson et al., 1996, Xenobiotica 26:559). A 3,4-dimethoxyacridine derivative having in position 9 a hydroxyethylamino substituent was found to be less potent than the corresponding dimethylaminoethylamino compound (Monge, A. et al., 1994, J. Heterocyclic Chem. 31:1455).

Acridine multi-substituted derivatives possessing nitro, methoxy, methyl, aminoalkylamino or hydroxyalkylamino substituents are known, and some have been studied as potential anticancer agents (Horowska et al., 1968, Rocz. Chem. 42:1351; Steck, E. A. et al., 1957, J. Am. Chem. Soc. 79:4414; Monge. et al., 1994, J. Heterocyclic Chem. 31:1455; Wilson et al., 1989, J. Med Chem. 32:23; Wysocka-Skrzela et al., 1981, Pol. J. Chem. 55:2211; Cholody, et al., 1983, Pol. J. Chem. 57:285; Cain et al., 1974, J. Med. Chem. 173:922; Cholody, et al., 1991, J. Heterocyclic Chem. 28: 209; U.S. Pat. No. 2,762,809; Yekundi, et al., 1957, *Chem. Ber.* 90:2448). However, the effectiveness of these compounds in inhibiting tumor growth varies.

There is a need for more nontoxic and effective antitumor agents. An objective of the present invention is to provide novel 9-alkylamino-1-nitroacridine derivatives as anticancer agents with an enhanced therapeutic index.

SUMMARY OF THE INVENTION

The invention is directed to novel 1-nitroacridine derviative(s), to methods for their preparation, as well as compositions comprising such derivatives. The invention is also directed to methods of using such derivatives and compositions to inhibit or prevent growth of tumors and/or prevent or inhibit metastases in a mammal, particularly a human patient by administering to such mammal an amount of said derivatives or compositions effective to inhibit or prevent growth of a tumor(s) and/or prevent or inhibit metastases in said mammal. The invention is further directed to the use of these derivatives for the manufacture of a medicament for prevention or inhibition of tumor growth and/or prevention of metastases. In a particular embodiment, the tumor is selected from the group consisting of prostate tumor, colon tumor, lymphoma, breast tumor, leukemia, and/or sarcoma. In a most particular embodiment, the tumor is a prostate tumor.

The invention is additionally directed to methods of using such derivatives and compositions to inhibit or prevent viral, parasite, bacteria (e.g., Staphylococcus, Streptococcus, Niseria), and/or fungal growth or infection comprising administering to a mammal, particularly a human patient an amount of said derivatives and compositions effective to inhibit or prevent microorganism, particularly, viral, bacterial, parasite and/or fungal growth or infection. The invention is further directed to the use of these derivatives for the manufacture of a medicament for prevention or inhibition of viral, bacterial, parasite and/or fungal growth or infection.

The derivative of the present invention has the structure,

I

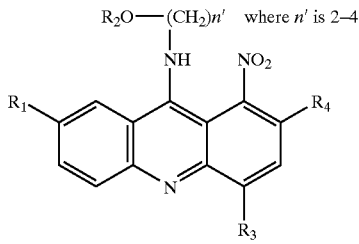

wherein when $R_1$ is H, $R_2$ is H or $CO(CH_2)_nCH_3$, where n=1–8, $R_3$ is H, $(CH_2)_nCH_3$, where n=0–1 or $O(CH_2)_nCH_3$, where n=0–1 and $R_4$ is H, $(CH_2)_nCH_3$, or $O(CH_2)_nCH_3$, where n=0–1;

wherein when $R_1$ is $O(CH_2)_nCH_3$, where n=0–1, and $R_2$ is H, $R_3$ and $R_4$ is H and wherein when $R_1$ is $O(CH_2)_nCH_3$, where n=0–1 and $R_2$ is $CO(CH_2)_nCH_3$, where n=1–8, $R_3$ is H, $(CH_2)_nCH_3$, where n=0–1 or $O(CH_2)_nCH_3$, where n=0 –1, and $R_4$ is H, $(CH_2)_nCH_3$, or $O(CH_2)_nCH_3$, where n=0–1 or salts thereof.

Examples of salts include but are not limited to the acid-addition salts, particularly, the non-toxic, acid addition salts. Acids useful for preparing the acid-addition salts include, inter alia, inorganic acids, such as hydrohalic acids (e.g. hydrochloric acid and hydrobromic acid), sulfuric acid and organic acids, such as lactic, methanesulfonic acid, oxalic, maleic, tartaric, citric, acetic and succinic acid.

In a specific embodiment, the 1-nitroacridine derivatives are selected from the group consisting of 9-(2'-hydroxyethylamino)-4-methyl-1-nitroacridine, 9-(2'- hydroxyethylamino)-7-methoxy-1-nitroacridine, 9-(2'-hydroxyethylamino)-7-methoxy-4-methyl-1-nitroacridine, 9-(2'-acetoxyethylamino)-1-nitroacridine, 9-(2'-propionoxyethylamino)-1-nitroacridine, 9-(3'-hydroxypropylamino)-7-methoxy-1-nitroacridine, 9-(3'-hydroxypropylamino)-4-methyl-1-nitroacridine, 9-(2'-acetoxyethylamino)-4-methyl-1-nitroacridine, 9-(2'-propionoxyethylamino)-4-methyl-1-nitroacridine, 9-(3'-acetoxypropylamino)-4-methyl-1-nitroacridine, 9-(2'-propionoxypropylamino)-4-methyl-1-nitroacridine, 9-(2'-hydroxyethylamino)-4-methoxy-1-nitroacridine, 9-(3'-hydroxypropylamino)-4-methoxy-1-nitroacridine, 9-(4'-hydroxybutylamino)-4-methoxy-1-nitroacridine, 9-(4'-hydroxybutylamino)-7-methoxy-1-nitroacridine and 9-(2'-acetoxyethylamino)-7-methoxy-4-methyl-1-nitroacridine, 9-(3'-hydroxypropylamino)-7-methoxy-4-methyl-1-nitroacridine, 9-(4'-hydroxypropyl amino)-7-methoxy-4-methyl-1-nitroacridine, 9-(3'-acetoxypropylamino)-7-methoxy-4-methyl-1-nitroacridine, 9-(2'-butyloxyethylamino)-4-methyl-1-nitroacridine,

DETAILED DESCRIPTION OF THE INVENTION

Synthetic Methods

Figure 1:
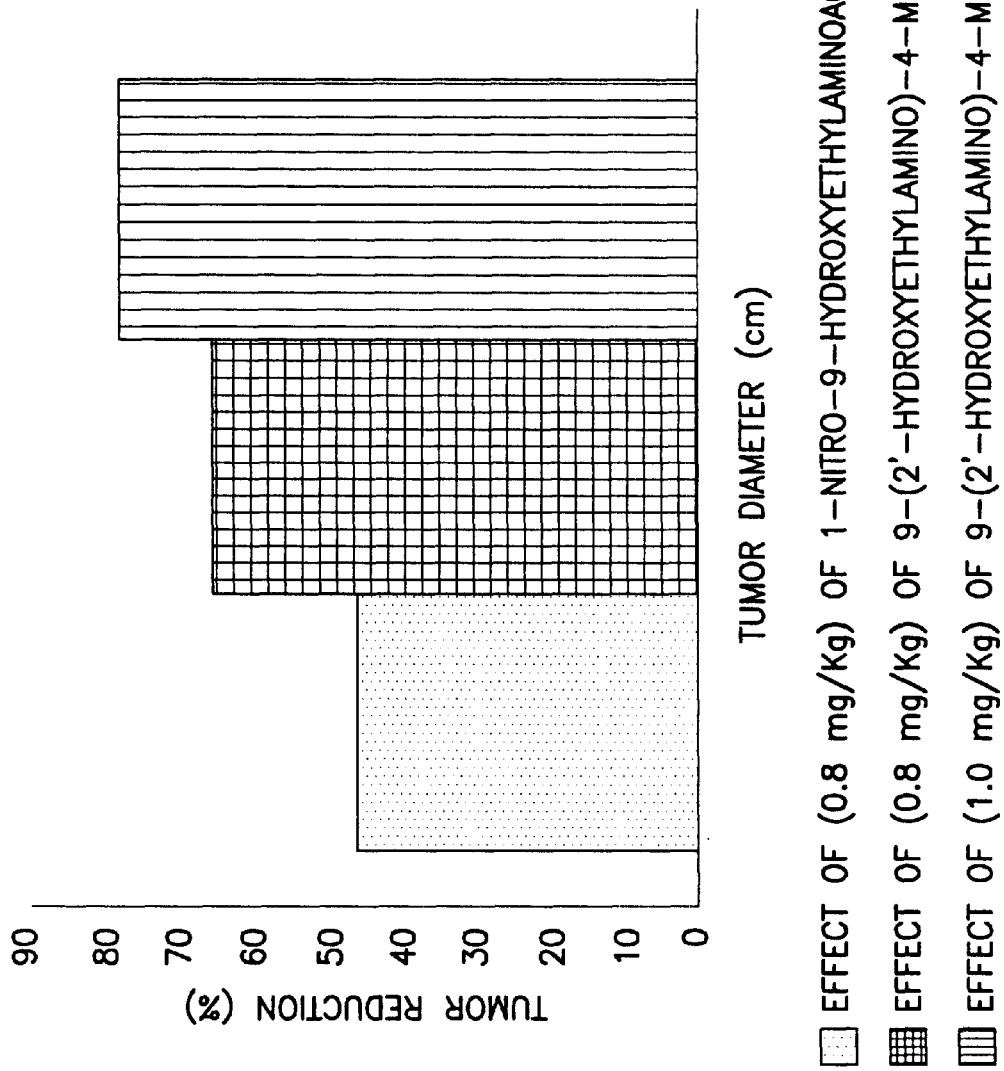
FIG. 1 compares the antitumor effect of 1-nitro-9-hydroxyethylaminoacridine and 9-(2'-hydroxyethylamino)-4-methyl-1-nitroacridine in Copenhagen rats. □ Shows the effect of (0.8 mg/Kg) of 1-nitro-9-hydroxyethylaminoacridine, ▦ shows the effect of (0.8 mg/Kg) of 9-(2'-hydroxyethylamino)-4-methyl-1-nitroacridine and ▥ shows the effect of (1.0 mg/Kg) of 9-(2'-hydroxyethylamino)-4-methyl-1-nitroacridine.

The compounds of this invention are prepared by a series of reactions as shown on Scheme 1

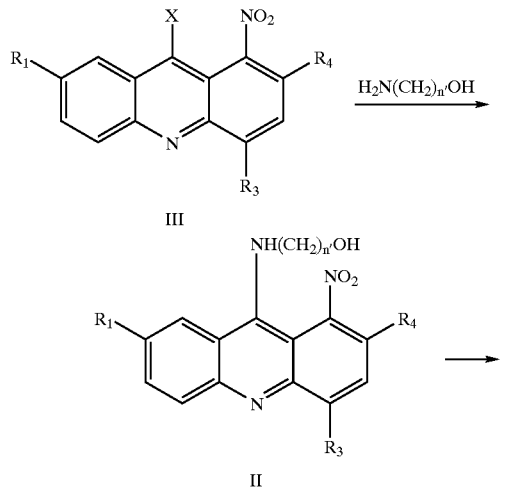

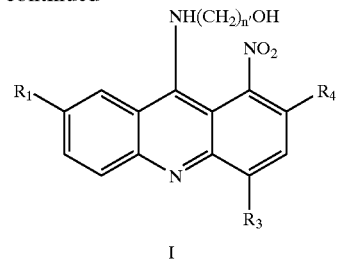

where $R_1$–$R_4$ are as hereinbefore defined and X is Cl, phenoxy or pyridinium salt, The compound III which may be employed as starting material in the practice of the present invention may be prepared in accordance with the teaching set forth in Ledochowski, A. *Mat. Med. Pol.* 1976, 3:237 for 9-amino-1-nitroacridine derivatives ($R_1$=$R_3$=H); in Yekundi, K. G. et al *Chem. Ber.* 1957, 90:2448 for 9-amino-7-methoxy-1-nitroacridines ($R_1$=OCH$_3$, $R_3$ =H); and in Horowska, B.; Ledóchowski, A. *Rocz. Chem.* 1968, 42:1351 for 9-amino-4-methyl or 4-methoxy-1-nitroacridines ($R_1$=H, $R_3$=OCH$_3$ or CH$_3$). A method for obtaining III (9-amino-7-methoxy-4-methyl-1-nitroacridines) is presented on the Scheme 2.

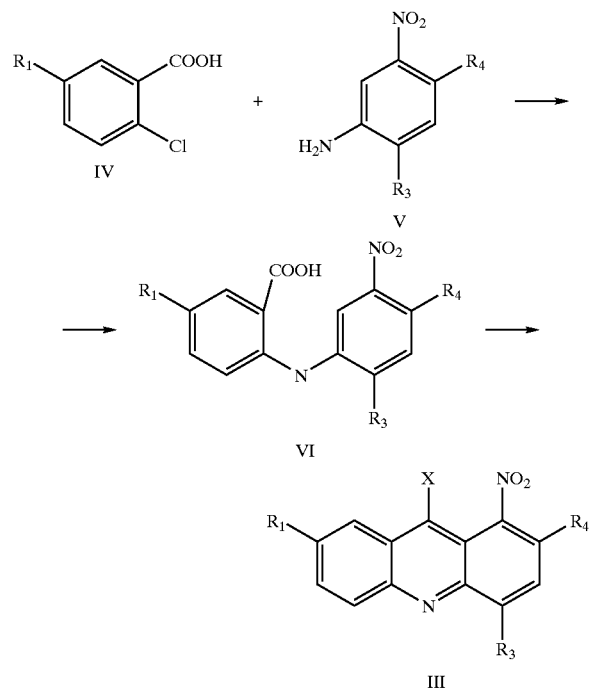

The substituted 1-nitroacridines of this invention of general formula II may be prepared by condensation of an appropriate substituted o-halogenobenzoic acid and aniline derivative or alternatively, of substituted anthranilic acid and halogenobenzene derivative, the condensation being affected by heating at least equimolar amounts of the reactants in the presence of an acid acceptor and catalytic amounts of copper or/and its salts. Preferably, the benzoic acid derivatives may be used as their salts with alkali metals, such as sodium or potassium salts. The heating of the reactants takes place without a solvent or in a suitable solvent at temperatures from 80 to 180° C. Suitable solvents include but are not limited to such organic solvents as dimethylformamide, dimethylacetamide, diphenyl ether, nitrobenzene, and higher aliphatic alcohols, such as amyl alcohol. Suitable acid acceptors include tertiary amines and alkali metals salts, such as sodium and potassium carbonates and the like. If desired, the reaction solvent itself may serve as the acid acceptor, such as when the dimethylaniline is employed as the solvent. The desired condensation product of general formula VI is preferably separated as a solution of its salt in water, and precipitated by an addition of mineral acid, such as hydrochloric acid. The desired product is then removed from the aqueous mixture by filtration, and optionally, purified by usual techniques, such as crystallization from a suitable organic solvent. The condensation products of general formula VI may be cyclized to the acridine derivative by usual methods known in the art (Acheson, R. M. Ed., Acridines, Interscience Publishers, NY, London, 1973). In a preferred embodiment of the cyclization, N-phenylanthranilic acid derivative is heated in a solution of phosphorous oxychloride at temperature from 60° C. to reflux, an excess of the reactant is removed by evaporation, and the product isolated by precipitation or extraction using a suitable solvent. Suitable solvents include such organic solvents as chloroform, methylene chloride, benzene, toluene or ether. The formed 9-chloroacridine derivative III is further isolated and purified by the usual techniques. When $R_3$ is H, two isomers are formed. The isomers may be separated by heating III where X=Cl to give pyridinium salts of III which can easily be separated. Those isomers are heated with phenol and give III, where X=OPh.

A method of this invention for obtaining 1-nitro-9-(hydroxyalkylamino)acridine derivatives or their salts of the formula II, wherein substituents $R_1$ and $R_3$ are as hereinbefore defined, comprises reacting a suitable 9-chloro-derivative of formula III or related 9-phenoxy-derivative or related acridinyl-9 pyridinium salt with an appropriate derivative of hydroxyalkylamine in phenol at temperatures from 40 to 120° C. The desired product is then isolated by precipitation of its salt with non-polar organic solvent. Suitable organic solvents include ethyl ether, benzene, toluene, tetrahydrofurane. Alternatively, the desired product may be isolated by alkalization of the reaction mixture and extraction of the product with a suitable, water immiscible solvent. The suitable, water immiscible solvents include ethyl ether, benzene, toluene, chloroform, ethyl acetate and the like.

Alternatively, condensation of suitable 9-chloro-derivative of formula III or related 9-phenoxy-derivative or related acridinyl-9 pyridinium salt with an appropriate derivative of hydroxyalkylamine may be performed in a suitable polar solvent in a presence of acidic catalyst. Suitable polar solvents include alcohols, polar aprotic solvents or hydroxyalkylamine itself. Suitable acidic catalyst include mineral acids, strong organic acids or phenol.

A method of this invention for obtaining 1-nitro-9-(alkoxyalkylamino)acridine derivatives or their salts of the formula I, wherein substituents $R_1$-$R_4$ are as hereinbefore defined, comprises reacting of suitable 1-nitro-9-(hydroxyalkylamino)acridine derivative with a suitable acylating agent. A suitable acylating agent includes but is not limited to carboxylic acids, related acid chlorides, acid anhydrides or others known in the art. In a preferred embodiment of the reaction in the present invention, acylating agent is formed from carboxylic acid in situ in the reaction mixture. The reaction is preferably conducted in suitable solvents. Suitable solvents include organic solvents such as haloalkanes, e.g., chloroform, aromatic hydrocarbons, e.g. benzene and toluene, aliphatic ethers or aliphatic cyclic ethers, or carboxylic acids, preferably the same acid which serves as the acylating agent. The condensation is typically done at low temperature, preferably from −30° C. to room temperature, and products are isolated by usual methods.

The compounds of the present invention may also be chemically linked to one or more moieties or conjugates which enhance the activity, cellular distribution, targetting or uptake of the compound of the present invention. These moieties may include but are not limited to peptides, antibodies, proteins, nucleic acids, and adenoviruses. In a specific embodiment, the compound of the present invention may be conjugated to a tumor cell targeting protein or polypeptide using the procedures described in U.S. Pat. No. 5,759,514.

Compositions

An effective therapeutic amount of this mixture is alone, or in combination with pharmaceutically acceptable carriers, formulated into the pharmaceutical formulation suitable for parenteral or oral administration which can be parenterally or orally administered to inhibit the growth of a tumor in a mammal and particularly a human. The composition may also be administered topically to cutaneous lesions. Parenteral administration includes intravenous, intraarterial, subcutaneous, intraperitoneal or intramuscular injection or infusion; or intracranial, e.g., intrathecal or intraventricular, administration. The specific cancers which can be treated with the composition of the present invention can include but is not limited to prostate cancer, colon cancer, lymphoma, breast cancer, leukemia, sarcoma and/or lymphoma.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The compositions of the present invention may comprise a "pharmaceutically acceptable carrier" or "excipient". Such a carrier or excipient is a pharmaceutically acceptable solvent, suspending agent or any other pharmacologically inert vehicle for delivering one or more of the compounds of the present invention to an animal. The excipient may be liquid or solid and is selected, with the planned manner of administration in mind, so as to provide for the desired bulk or consistency, when combined with the compound of the present invention and the other components of a given pharmaceutical composition. Typical pharmaceutical carriers include, but are not limited to, binding agents (e.g., pregelatinized maize starch, polyvinylpyrrolidone or hydroxypropyl methylcellulose); fillers (e.g., lactose and other sugars, microcrystalline cellulose, pectin, gelatin, calcium sulfate, ethylcellulose, polyacrylates or calcium hydrogen phosphate); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate); disintegrants (e.g., starch, sodium starch glycolate); and wetting agents (e.g., sodium lauryl sulphate).

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

Emulsions are typically heterogeneous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug that may be present as a solution in the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. One major type of liposomal composition includes phospholipids other than naturally derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Although the effective amount of the composition according to the present invention can be varied depending upon various factors including the subject to be administered, severity of cancer to be treated, etc., generally in an adult man (based on a body weight of 60 kg), the dosage may be in the range of about 0.5 to about 2 mg/kg of body weight per day for oral administration, about 0.2 to about 1 mg/kg of body weight per day for intravenous administration and in the range of about 0.1 to about 0.5 mg/kg of body weight, per day, for intramuscular injections.

The composition of the present invention can include other medicinal components having immunoadjuvant activity or anti-cancer activity, or can be administered in combination with another immunoadjuvant or anti-cancer agent. As the immunoadjuvant which can be included in, or combined with, the composition according to the present invention, the following can be mentioned: monoclonal antibodies, immunoagitators, human immunoglobulins or cytokines, such as interferons or interleukins, or sugar specific proteins, such as lectins. As the anti-cancer agent which can be used for this purpose, the following can be mentioned: synthetic anti-cancer agents, for example, alkylating agents such as chlorambucil, melphalan, cyclophosphamide, nitrosourea amine compounds such as mannomustine, ethylenediamines such as uredepa; antimetabolic agents, for example, folic acid antagonists such as methotrexate, aminopterine, purine antagonists such as mercaptopurine, pyrimidine antagonists such as proxuridine, 6-azauridine, sugar-based antagonists such as mitobronitol, or cisplatin, picivanil, 5-fluorouracil (5-FU), anti-cancer antibiotics, for example, actinomycin, THP-adriamycin, mitomycin, hormone antagonists such as tamoxifen, and alkaloid plant components such as demecolcine. Additionally, the composition of the present invention may comprise more than one 1-nitroacridine derivative.

EXAMPLES

Synthesis of Compounds

1-Nitro-9-Hydroxyethylaminoacridine

This compound is synthesized generally using the methods described in EP 38579. Specifically, 2 g of 2-aminoethanol hydrochloride is added to 6.4 g of 1-nitro-9-phenoxyacridine dissolved in 20 g of freshly distilled phenol. The mixture is heated for 40 minutes at a temperature of 80° C. and then cooled, diluted with ether. It is then poured into a dry ether which was acidified with an ethereal solution of hydrogen chloride. The orange colored precipitate of 1-nitro-9-(2-hydroxyethylamino)-acridine hydrochloride, obtained in this way is filtered and crystallized from dry ethanol. The melting point of the compounds obtained was 170° C., with decomposition. Yield 91%. Elementary analysis for the formula: $C_{15}H_{14}N_3O_3Cl$: calculated: 56.47% C, 4.42% H, 13.17% N; determined: 56.44% C, 4.40% H, 13.03% N

9-(2'-hydroxyethylamino)-4-methyl-1-nitroacridine

4-Methyl-1-nitro-9-phenoxyacridine (0.33 g) is dissolved in phenol (10 g), ethanolamine hydrochloride (0.2 g) is added and the mixture is heated at 80° C. for 0.5 hour. The reaction mixture is cooled to room temperature, diluted with ether, slowly poured into dry ether (200 ml) and acidified with ethereal solution of hydrogen chloride. The resulting precipitate is filtered off, washed with ether and crystallized from absolute ethanol to give 9-(2'-hydroxyethylamino)-4-methyl-1-nitroacridine monohydrochloride as orange crystals (0.27 g, 84%), m.p. 238° C. (decomp.) $^1$H NMR ($d_6$ DMSO): δ2.45 (s, 3H, $CH_3$), 3.48 (q, 2H, H–2'), 3.65 (t, 2H, H–1'), 4.3 (t, 1H, OH), 7.1 (t, 1H, H–7), 7.24 (d, 1H, J=7.8 Hz, H–2), 7.35 (d, 1H, J=7.8 Hz, H–3), 7.5 (t, 1H, H–6), 7.65 (d, 1H, J=8 Hz, H–5), 7.75 (d,1H, J=8.0 Hz, H–8).

9-(2'-hydroxyethylamino)-7-methoxy-4-methyl-1-nitroacridine

7-Methoxy-4-methyl-1-nitro-9-phenoxyacridine (0.72 g) is dissolved in phenol (20 g). Ethanolamine hydrochloride (0.2 g) is added and the mixture is heated at 80° C. for 1.5 hour. The reaction mixture is cooled to room temperature, diluted with dry ether, slowly poured into dry ether (300 ml) and acidified with ethereal solution of hydrogen chloride. The resulting precipitate is filtered off, washed twice with ether and crystallized from absolute methanol to give 9-(2'-hydroxyethylamino)-7-methoxy-4-methyl-1-nitroacridine monohydrochloride as orange crystals (0.6 g, 86%), m.p. 200° C. (decomp.) $^1$H NMR ($d_6$ DMSO): δ2.60 (s, 3H, $CH_3$), 3.50 (s, 4H, H–1', H–2'), 4.00 (s, 3H, $OCH_3$), 7.66 (dd, 1 H, $J_1$=9.3 Hz, $J_2$=2.5 Hz, H–6), 7.85 (d, 1 H, J=8.2 Hz, H–3), 8.02 (s, 1 H, H–8), 8.15 (d, 1 H, J=7.8 Hz, H–2), 8.22 (d, 1 H, J=7.8 Hz, H–5).

9-(2'-hydroxyethylamino)-7-methoxy-1-nitroacridine

7-Methoxy-1-nitro-9-phenoxyacridine (0.69 g) is dissolved in phenol (20 g). Ethanolamine hydrochloride (0.2 g) is added and the mixture is heated at 100° C. for 1.5 hour. The reaction mixture is cooled to room temperature, diluted with dry ether (100 ml), slowly poured into dry ether (300 ml) and acidified with ethereal solution of hydrogen chloride. The resulting precipitate is filtered off, washed twice with ether and crystallized from absolute methanol-ether to give 9-(2'-hydroxyethylamino)-7-methoxy-1-nitroacridine monohydrochloride (0.58 g, 83% yield), m.p. 220° C. (decomp.) $^1$H NMR ($d_6$ DMSO): δ3.45 (t, 2 H, H–2'), 3.65 (t, 21H, H–1'), 3.80 (s, 3 H, $OCH_3$), 7.30 (dd, 1H, $J_1$ =9.3 Hz, $J_2$=2.5 Hz, H–6), 7.35 (d, 1 H, J=2.5 Hz, H–8), 7.40 (d, 1 H, J=9.3 Hz, H–5), 7.7 (m, 2 H, H–3, H–4), 7.87 (m, 1H, H–2).

9-(2'-Acetoxyethylamino)- 1-nitroacridine

Thionyl chloride (7.5 ml) is added to a stirred, cooled to –20° C. acetic acid (30 ml). Next, at the same temperature, 9-(2'-hydroxyethylamino)-1-nitroacridine (0.5 g) is added in portions, and the mixture is stirred at room temperature for 24 hours. The solvent is distilled off under reduced pressure, the residue washed several times with 10% aqueous sodium bicarbonate and water, dried under vacuum, and crystallized from absolute ethanol-ethereal hydrogen chloride solution to give 9-(2'-acetoxyethylamino)-1-nitroacridine (0.4 g, 80% yield), m.p. 170–2° C. (decomp.). $^1$H NMR ($d_6$ DMSO): δ1.6 (s, 3 H, $CH_3$), 3.85 (t, 2 H, H–1'), 4.2 (t, 2 H, H–2'), 7.10 (t, 1 H, H–7), 7.25 (d, 1 H, J=7.5 Hz, H–2), 7.35 (d, 1H, J=7.8 Hz, H–5), 7.42 (d, 1 H, J=8.3 Hz, H–4), 7.50 (d, 1 H, J=7.5 Hz, H–3), 7.60 (d, 1 H, J=7.8 Hz, H–6), 7.82 (d, 1 H, J=7.8 Hz, H–8).

9-(3'-Hydroxypropylamino)-7-methoxy-1-nitroacridine

7-Methoxy-1-nitro-9-phenoxyacridine (0.69 g) is dissolved in phenol (20 g), 3-aminopropanol hydrochloride is added and the mixture is heated at 100° C. for 1.5 hour. The reaction mixture is cooled to room temperature, diluted with dry ether (100 ml), and slowly poured into dry ether (300 ml) preacidified with ethereal solution of hydrogen chloride. The resulting precipitate is filtered off, washed twice with ether and crystallized from absolute methanol-ether (3:1) to give 9-(3'-hydroxypropylamino)-7-methoxy-1-nitroacridine monohydrochloride as orange crystals (0.5 g, 72% yield), m.p. 208–210° C. (decomp.) $^1$H NMR ($d_6$ DMSO): δ1.75 (t, 2H, H–2'), 3.45 (q, 2 H, H–3'), 3.74 (t, 2 H, H–1'), 4.32 (t, 1 H, OH), 7.15 (dd, 1 H, $J_1$=2.7 Hz, $J_2$=9.0 Hz, H–6), 7.20 (d, 1 H, J=9.5 Hz, H–2), 7.25 (d, 1 H, J=9.3 Hz, H–5), 7.3 (d, 1H, J=7.7 Hz, H–8), 7.45 (t, 1 H, H–3).

9-(2'-Propionoxyethylamino)-1-nitroacridine

Thionyl chloride (8 ml) is added to a stirred, cooled to –20° C. propionic acid (60 ml). Next, at the same temperature, 9-(2'-hydroxyethylamino)-1-nitroacridine (0.5 g) is added in portions, and the mixture is stirred at room temperature for 24 hours. The solvent is distilled off under reduced pressure, the residue washed several times with 10% aqueous sodium bicarbonate and water, dried under vacuum, and crystallized from absolute ethanol-ethereal hydrogen chloride solution to give the acid addition salt, 9-(2'-propionoxyethylamino)-1-nitroacridine hydrochloride as yellow crystals (0.37 g, 65% yield), m.p. 98–100°C. $^1$H NMR (NMR of the free base) ($d_6$ DMSO): δ1.00 (t, 3 H, H–3"), 2.30 (q, 2 H, H–2"), 3.90 (t, 2 H, H–1'), 4.20 (t, 2H, H–2'), 7.10 (t, 1 H, H–7), 7.25 (d, J=8.8 Hz, H–2), 7.30 (d, 1 H, J=8.3 Hz, H–5), 7.36 (d, 1 H, J=9.3 Hz, H–4), 7.38, (t, 1 H, H–3), 7.51 (t, 1 H, H–6), 7.82 (d, 1 H, J=7.3 Hz, H–8), 10.84 (s, 1 H, NH).

9-(2'-Hydroxyethylamino)-4-methoxy-1-nitroacridine

4-Methoxy-1-nitro-9-phenoxyacridine (0.346 g) is dissolved in phenol (30 g), ethanolamine hydrochloride (0.12 g) is added and the mixture is heated at 80° C. for 1.5 hour. The reaction mixture is cooled to room temperature, diluted with dry ether (20 ml), slowly poured into dry ether (200 ml) and acidified with ethereal solution of hydrogen chloride. The resulting precipitate is filtered off, washed several times with ether and crystallized from absolute ethanol-ether (5:1) to give 9-(2'-hydroxyethylamino)-4-methoxy-1-nitroacridine monohydrochloride as yellow crystals (0.27 g, 77% yield), m.p. 210–212° C. (decomp.) 1H NMR (for a free base) ($d_6$ DMSO): δ10.18 (s, 1 H, NH), 7.78 (d, 1 H, J=7.8 Hz, H–8), 7.67 (d, 1 H, J=8.3 Hz, H–5), 7.47 (t, 1 H, J=7.8 Hz, H–6), 7.36 (d, 1 H, J=8.8 Hz), 7.10 (m, 2H, H–3, H–7), 4.31 (t, 1 H, J=5.4 Hz, OH), 3.70 (t, 2 H, J=6.4 Hz, H–1'), 3.64 (q, 2H, J=6.3 Hz, H–2').

9-Chloro-7-methoxy-4-methyl-1-nitroacridine

N-(2'-methyl-5'-nitrophenyl)-5-methoxyanthranilic acid (7.2 g) is heated in phosphorous oxychloride (60 ml) at 120° C. for 1 hour. Excess phosphorous oxychloride is distilled off under reduced pressure, and the residue poured slowly into a stirred mixture of chloroform, concentrated ammonium hydroxide and ice. The separated chloroformic layer is washed with water and dried using magnesium sulfate. Chloroform is evaporated to dryness, and the residue is crystallized from benzene to give 9-chloro-7-methoxy-4-methyl-1-nitroacridine (6.1 g, 68% yield), m.p. 227–228° C. 1H NMR ($d_6$ DMSO): δ8.23 (d, 1 H, J=9.3 Hz), 8.13 (d, 1 H, J=7.3 Hz), 7.79 (bd, 1 H, J=8.3 Hz), 7.71 (dd, 1H, $J_1$=9.3 Hz, $J_2$=2.9 Hz), 7.58 (d, 1 H, J=2.9 Hz), 4.02 (s, 3 H), 2.85 (s, 3 H).

N-(2'-methyl-5'-nitrophenyl)-5-methoxyanthranilic acid

Potassium salt of 2-bromo-5-methoxybenzoic acid (23 g) and 2-methyl-5-nitroaniline (40 g) are stirred and heated at 110° C. in the presence of 50 mg of catalytic copper for 50 minutes. Next, the reaction mixture is poured on 5% solution of potassium hydroxide in water (600 ml) and cooled. The formed precipitate is filtered off, washed with water, and the collected solutions are acidified with hydrochloric acid to pH 5. The formed solid is filtered off and crystallized from methanol-acetone (2:1) to give N-(2'-methyl-5'-nitrophenyl)-5-methoxyanthranilic acid (11.2 g, 56% yield), m.p. 219–221° C. $^1$H NMR ($d_6$ DMSO): δ9.20 (bs, 1H), 7.88 (d, 1 H, J=1.9 Hz), 7.65 (dd, 1 H, $J_1$=7.8 Hz, $J_2$=1.9 Hz), 7.44 (d, 1 H, J=8.3 Hz), 7.43 (d, 1 H, J=2.9 Hz), 7.26 (d, 1 H, J=8.8 Hz), 7.19 (dd, 1H, $J_1$=8.8 Hz, $J_2$=2.9 Hz), 3.68 (s, 3 H), 2.27 (s, 3 H).

9-(3'-hydroxypropylamino)-4-methyl-1-nitroacridine

4-Methyl-1-nitro-9-phenoxyacridine (0.66 g) is dissolved in phenol (15 g), 3-aminopropanol hydrochloride is added and the mixture is heated at 80° C. for 1.5 hour. The reaction mixture is cooled to room temperature, diluted with dry ether (50 ml) and acidified with ethanol solution of hydrogen chloride. The resulting precipitate is filtered off, washed several times with ether and crystallized from absolute ethanol to give the acid addition salt, 9-(3'-hydroxypropylamino)-4-methyl-1-nitroacridine hydrochloride as yellow crystals (0.54 g, 76% yield), m.p. 205–206° C., anal. $C_{17}H_{18}N_3O_3Cl$ (C, H, N). $^1$H NMR ($D_2O$): δ1.65 (m, 2H, H–2'), 2.40(s, 3H, $CH_3$), 3.20(q, 2H, H–3'), 3.40(m, 2H, H–1'), 7.22(t, 1H, H–7), 7.48(d, 1H, J=7.8 Hz, H–3), 7.48(d, 1H, J=7.8 Hz, H–3), 7.54(d, 1H, J=8.3 Hz, H–6), 7.60(t, 1H, H–5), 7.74(t, 1H, H–8).

9-(2'-acetoxyethylamino)-4-methyl-1-nitroacridine

Thionyl chloride (8 ml) is added to a stirred, cooled to –20° C. acetic acid (30 ml). At the same temperature 9-(2-hydroxyethylamino)-4-methyl-1-nitroacridine hydrochloride (0.6 g) is added in portions. The reaction mixture is stirred at room temperature for 20 hours. Next, the solvent is distilled off under reduced pressure, the residue washed several times with 10% aqueous sodium dicarbonate and water, dried under vacuum and crystallized from dry methanol-ether solution to give 9-(2'-acetoxyethylamino)-4-methyl-1-nitroacridine (72% yield), m.p. 210–212° C., anal. $C_{18}H_{18}N_3O_4Cl$ (C, H, N). $^1$H NMR ($D_2O$): δ2.45 (s, 3H, $CH_3$'), 2.6(s, 3H $CH_3$), 3.25(t, 2H, H–1'), 3.65(t, 2H, H–2'), 7.35(t, 1H, H–7), 7.58(d, 1H, J=8.8 Hz, H–2),7.66(d, 1H, J=8.3 Hz, H–3),7.7(t, 1H, H–6), 7.84(d, 1H, J=7.8 Hz, H–5), 7.9(d, 1 H, J=8.1 Hz, H–8).

9-(2'-propionoxyethylamino)-4-methyl-1-nitroacridine

Thionyl chloride (10 ml) is added to a stirred, cooled to –20° C. propionic acid (50 ml) and at the same temperature 9-(2-hydroxyethylamino)-4-methyl-1-nitroacridine (0.55 g) is added in portions, and the mixture is stirred at room temperature for 20 hours. The reaction mixture is distilled off under reduced pressure, washed several times with 10% aqueous sodium dicarbonate and water, dried under vacuum, and crystallized from absolute methanol-ethanol hydrogen chloride solution to give the acid addition salt, 9-(2-propionoxyethylamino)-4-methyl-1-nitroacridine hydrochloride with 68% yield, m.p. 228–230° C., anal. $C_{19}H_{19}N_3O_4Cl$ (C, H, N). $^1$H NMR ($d_6$ DMSO): δ1.20(t, 3H, H–3"), 2.0(q, 2H, H–2"), 2.8(s, 3H, $CH_3$), 3.9(t, 2H, H–1), 4.0(t, 2H, H–2'), 7.4(t, 1 H, H–7), 7.5(d, 1 H, J=7.8 Hz, H–3), 7.6(d, 1 H, J=8.3 Hz, H–6), 8.0(t, 1 H, H–5), 8.4(m, 1 H, H–8).

9-(2'-acetoxypropylamino)-4-methyl-1-nitroacridine

Thionyl chloride (20 ml) is added to a cooled to –20° C. and stirred acetic acid (35 ml) and at the same temperature 9-(3'-hydroxypropylamino)-4-methyl-1-nitroacridine (0.5 g) is added in portions. The reaction mixture is stirred at room temperature for 24 hours. The solvent is distilled off under reduced pressure, the residue washed several times with 10% aqueous sodium dicarbonate and water, dried under vacuum and crystallized from absolute ethanol to give 9-(2'-acetoxypropylamino)-4-methyl-1-nitroacridine with 67% yield, m.p. 150–152° C., anal. $C_{19}H_{19}N_3O_4$ (C, H, N). $^1$H NMR ($d_6$ DMSO): δ1.20(t, 3H, H–3"), 1.75(t, 2H, H–2'), 2.4(s, 3H, $CH_3$), 4.0(t, 2H, H–1'), 7.1(t, 1H, H–7), 7.2(d, 1H, J=7.8 Hz, H–2), 7.4 (d, 1H, J=7.8 Hz, H–3), 748(t, 1H, H–6), 7.65(d, 1H, J=8.3 Hz, H–5), 7.7(d, 1H, J=8.3 Hz, H–8).

9-(3'-propionoxypropylamino)-4-methyl-1-nitroacridine

Thionyl chloride (25 ml) is added to a cooled to –20° C. and stirred propionic acid (40 ml) and at the same temperature, 9-(3-hydroxypropylamino)-4-methyl-1-nitroacridine hydrochloride (0.6 g) is added in portions. The reaction mixture is stirred at room temperature for 20 hours. The solvent is distilled off under reduced pressure, the residue (oil) washed several times with 10% aqueous sodium dicarbonate and water, dried under vacuum and crystallized from dry methanol acidified with ethanol solution of hydrogen chloride give the acid addition salt, 9-(3'-propionoxypropylamino)-4-methyl-1-nitroacridine hydrochloride (78% yield), m.p. 161–163° C., anal. $C_{20}H_{22}N_3O_1Cl$ (C, H, N). $^1$H NMR ($d_6$ DMSO): δ10 (t, 3H, H–3"), 2.35(q, 2H, H–2"), 2.5(s, 3H, $CH_3$), 4.30(t, 2H, H–1'), 7.15(t, 1H, H–7), 7.26(d, 1H, J=7.8 Hz, H–2), 7.38(d, 1H, J=7.8 Hz, H–3), 7.5(t, 1 H, H–6), 7.62(d, 1H, J=8.0 Hz, H–5), 7.8(d, 1H, J=8.2 Hz, H–8).

9-(3'-hydroxypropylamino)-4-methoxy-1-nitroacridine

9-Chloro-4-methoxy-1-nitro-9-acridine (0.4 g) is dissolved in phenol (20 g), 3-aminopropanol (1.5 g) is added and the mixture is heated at 80° C. for 1 hour. The reaction mixture is cooled, diluted with dry ether and acidified with ethanol solution of hydrogen chloride. The resulting precipitate is filtered off, washed with dry ether and crystallized from absolute methanol to give 9-(3-hydroxypropylamino)-4-methyl-1-nitroacridine hydrochloride crystals (74% yield), m.p. 180–183° C., anal. $C_{17}H_{18}N_3O_4Cl$ (C, H, N). $^1H$ NMR ($D_2O$): δ1.68(s, 2H, H–2'), 3.40(t, 2H, H–3'), 3.50(q, 2H, H–1'), 4.0(s, 3H, $OCH_3$), 7.0(d, 1 H, J=8.8 Hz, H–3), 7.27(t, 1H, H–7), 7.49(d, 1 H, J=8.3 Hz, H–5), 7.65(t, 1H, H–6), 7.77(d, 1H, J=8.3 Hz, H–8), 7.90(d, 1H, J=8.3 Hz, H–2).

9-(4'-hydroxybutylamino)-4-methoxy-1-nitroacridine

4-Methoxy-1-nitro-9-phenoxyacridine (0.34 g) is dissolved in 20 g of phenol, 4-hydroxyaminobutanol hydrochloride (0.15 g) is added and the mixture is heated at 110° C. for 1.5 hour. The reaction mixture is cooled to room temperature, diluted with dry ether, acidified with ethanol solution of hydrogen chloride. The precipitate is filtered, washed with dry ether and crystallized from absolute ethanol to give the acid addition salt, 9-(4'-hydroxybutylamino)-4-methoxy-1-nitroacridine hydrochloride (69% yield), m.p. 149–152° C., anal. $C_{18}H_{20}N_3O_4Cl$ (C, H, N). $^1H$ NMR ($D_2O$): δ1.25(t, 2H, H–2'), 3.3(q, 2H, H–4'), 3.4(t, 2H, H–1'), 4.0(s, 3H, $OCH_3$), 7.1(d, 1H, J=8.8 Hz, H–3), 7.5(d, 1H, J=8.8 Hz, H–5), 7.6(t, 1H, H–6), 7.7(d, 1H, J=7.3 Hz, H–8), 7.9(m, 1H, H–2).

9-(4'-hydroxybutylamino)-4-methoxy-1-nitroacridine

9-Chloro-7-Methoxy-1-nitro-9-acridine (0.37 g), 10 g phenol and 4-hydroxyaminobutanol (0.15 g) are heated at 120° C. for 1.5 hour. The reaction mixture is cooled to room temperature, diluted with dry ether and acidified with ethanol solution of hydrogen chloride. The resulting precipitate is filtered, washed with ether and crystallized from methanol-ether (3:1) acidified with ethanol solution of hydrogen chloride to give the acid addition salt, 9-(4'-hydroxybutylamino)-7-methoxy-1-nitroacridine hydrochloride with 81% yield, m.p. 153–155° C., anal. $C_{18}H_{20}N_3O_4Cl$ (C, H, N). $^1H$ NMR ($D_2O$): δ1.68(t, 2H, H–3'), 3.39(t, 2H, H–1'), 3.50(q, 2H, H–2'), 4.0(s, 3H, $OCH_3$), 7.04(d, 1H, J=8.8 Hz, H–3), 7.27(t, 1H, H–7), 7.49(d, 1H, J=8.3 Hz, H–5), 7.65(t, 1H, H–6), 7.80(d, 1 H, J=8.3 Hz, H–8), 7.90(d, 1H, J=8.8 Hz, H–2).

9-(2'-acetoxyethylamino)-7-methoxy-4-methyl-1-nitroacridine

Thionyl chloride (5 ml) is added to a stirred, cooled to –20° C. acetic acid (20 ml) and at the same temperature 9-(2'-hydroxyethylamino)-7-methoxy-4-methyl-1-nitroacridine hydrochloride (0.3 g) is added in portions, and the mixture is stirred at room temperature for 18 hours. The solvent is distilled of under reduced pressure, the residue washed several times with 10% aqueous sodium bicarbonate and water, dried under vacuum and crystallized from benzene to give 9-(2'-acetoxyethylamino)-7-methoxy-4-methyl-1-nitroacridine (82% yield), m.p. 145–148° C., anal. $C_{19}H_{19}N_3O_5Cl$ (C, H, N). $^1H$ NMR ($d_6$ DMSO): δ1.6(t, 3H, H–2'), 2.6(s, 3H, $CH_3$), 3.4(s, 4H, H–2', H–1'), 4.0(s, 3H, $CH_3$), 7.66(dd, 1H, $J_1$=9.3 Hz, $J_2$=2.5 Hz, H–6), 7.85(d, 1H, J=8.2 Hz, H–3), 8.00(s, 1H, H–8), 7.7(t, 1 H, H–6), 8.15(d, 1H, J=7.8 Hz, H–2), 8.20(d, 1H, J=7.8 Hz, H–5).

9-(3'-Hydroxypropylamino)-7-methoxy-4-methyl-1-nitroacridine

7-Methoxy-4-methyl-1-nitro-9-phenoxyacridine (0.34 g) is dissolved in phenol (20 g), 3-hydroxypropylamine hydrochloride (0.15 g) is added and the mixture is heated at 90° C. for 2.5 hour. The reaction mixture is cooled to room temperature, poured to dry ether and acidified with ethanol solution of hydrogen chloride. The yellow precipitate is filtered, washed with ether and crystallized from dry methanol to give the acid addition salt, 9-(3'-hydroxypropylamino)-7-methoxy-4-methyl-1-nitroacridine hydrochloride (59% yield), m.p. 222–224° C. (decomp.) anal. $C_{18}H_{20}N_3O_4Cl$ (C, H, N). $^1H$ NMR ($D_2O$): δ1.83 (s 2H, H–2'), 2.5 (s, 3H, $CH_3$), 3.2 (t, 2 H, H–3'), 3.6 (quartet, 2H-H–1'), 3.8(s, 3H, $OCH_3$), 7.3(s 1 H, H–8), 7.4 (d, 1 H, J=8 Hz, H–3), 7.7 (d, 1 H, J=10 Hz, H–5), 8.0 (d, 1 H, J=8 Hz, H–2).

9-(4'-hydroxypropylamino)-7-methoxy-4-methyl-1-nitroacridine

7-Methoxy-4-methyl-1-nitro-9-phenoxyacridine (0.74 g) is dissolved in phenol (40 g), 4-hydroxybutylamine hydrochloride (0.25 g) is added and the mixture is heated at 100° C. for 2.0 hour. The reaction mixture is cooled, diluted with dry ether and acidified with ethereal solution of hydrogen chloride. The precipitate is filtered, washed with ether and crystallized from absolute ethanol to give the acid addition salt, 9-(4'-hydroxypropylamino)-7-methoxy-4-methyl-1-nitroacridine hydrochloride (71% yield), m.p. 156–159° C. (decomp.), anal. $C_{19}H_{22}N_3O_4Cl$ (C, H, N). $^1H$ NMR ($d_6$ DMSO): δ1.21 (bm, 2H, H–3'), 1.73 (m, 2H, H–2'), 2.80 (s, 3H, $C4–CH_2$), 3.23 (t, 2H-H–4'), 3.46(m, 2H, H–1'), 4.0(s 3H, $OCH_3$), 7.62 (dd, 1 H, $J_1$=9.2 Hz, $J_2$=2.5 Hz, H–6), 7.83 (d, 1 H, J=7.8 Hz, H–3), 8.10 (d, 1H, J=7.8 Hz, H–2), 8.15 (bs, 1H, H–8), 8.44 (d, 1H, J=9.2 Hz, H–5).

9-(2'-Butyloxyethylamino)-4-methyl-1-nitroacridine

Thionyl chloride (30 ml) is added to a cooled to –20° C. and stirred butyric acid (40 ml) and at the same temperature and 9-(2'-hydroxypropylamino)-4-methyl-1-nitroacridine hydrochloride (0.6 g) is added in portions. The reaction mixture is stirred at room temperature for 30 hours. The solvent is distilled off under reduced pressure, the residue (oil) washed several times with 10% aqueous sodium dicarbonate and water, dried under vacuum and crystallized two times from absolute ethanol to give 9-(2'-butyloxypropylamino)-4-methyl-1-nitroacridine hydrochloride (66% yield), m.p. 171–2° C., anal. $C_{21}H_{24}N_3O_4Cl$ (C, H, N). $^1H$ NMR ($D_2O$): δ0.52 (t, 3H, H–4'), 0.77(bs, 2H, H–3"), 1.0 (s, 2H, H–2") 2.55 (s, 3H, $CH_3$), 2.63(bs, 2H, H–2'), 3.74(s, 1H, H–1'), 7.36(t, 1H, J=7.7 Hz, H–7), 7.63(d, 1H, J=7.7 Hz, H–6), 7.90(d, 1H, J=8.2 Hz, H–5), 7.93(d, 1H, J=7.7 Hz, H–8).

9-(3'-Acetoxyethylamino)-7-methoxy-4-methyl-1-nitroacridine

Thionyl chloride (20 ml) is added to a stirred, cooled to –20° C. acetic acid (40 ml) and at the same temperature. 9-(3'-Hydroxypropylamino)-7-methoxy-4-methyl-1-nitroacridine hydrochloride (0.84 g) is added in portions, and the mixture is stirred at room temperature for 24 hours. The solution is distilled off under reduced pressure, the residue washed several times with 10% aqueous sodium bicarbonate and water, dried under vacuum, acidified with ethereal solution of hydrogen chloride and crystallized from absolute ethanol to give 9-(3'-acetoxypropylamino)-7-methoxy-4-methyl-1-nitroacridine (64% yield), m.p. 1163–165° C., anal. $C_{20}H_{22}N_3O_5Cl$ (C, H, N). $^1$H NMR ($d_6$ DMSO): δ1.65(s, 3H, $CH_3$"), 1.75 (t, 2H, H–2'), 2.5(s, 3H, C–4, $CH_3$), 3.5(quartet, 2H, H–3"), 3.76(t, 2H, H–1'), 3.9(s, 3H, C–7O$CH_3$). 7.4(s, 1H, H–8), 7.6 (d, 1H, J=8.0 Hz, H–3), 7.7(d, 1H, J=9 Hz, H–5), 7.95(d, 1H, J=8 Hz, H–2)

Antitumor activity against ascites adenocarcinoma Walker 256 in rats

Tumors are transplanted weekly into Wistar rats by intraperitoneal inoculation of $10^6$ tumor cells. In the experiments, Walker carcinosarcoma 256 cells are transplanted on day 0 in Wistar rats weighing 75–100 g. by i.p. injection of $10^6$ cells per animal. Each acridine is administered i.p. on days 3, 4, and 5 after tumor transplantation. Five rats are in each group at a given drug dose level and a group of 10 rats served as control for all test groups. Dose levels are separated usually by 0.3 log dose intervals from the inactive dose to the clearly toxic dose. Each acridine is tested at five different doses. The activity of the drug T/C (%) is expressed as % increase in mean survival time (in days) of test group (T) to the mean survival time (in days) of the control (C). Usually, the antitumor activity is presented only for the optimal dose (O.D. mg/kg/day) of tested compounds, at which the highest antitumor activity is observed.

The results are shown in Table 1 below:

TABLE I

| Compound | Optimal dose [mg/kg] | Antitumor activity against Walker256 (Survival) Test/Control [%] |
|---|---|---|
| 9-(2'-hydroxyethylamino)-4-methyl-1-nitroacridine | 4 | 217 |
| 9-(2'-hydroxyethylamino)-7-methoxy-1-nitroacridine | 2 | 150;200 |
| 9-(2'-hydroxyethylamino)-7-methoxy-4-methyl-1-nitroacridine | 16 | 233 |
| 9-(2'-acetoxyethylamino)-1-nitroacridine | 1 | 167 |
| 9-(2'-propionoxyethylamino)-1-nitroacridine | 1 | 200 |
| 9-(3'-hydroxypropylamino)-7-methoxy-1-nitroacridine | 0.5 | 182;229 |
| 9-(3'-hydroxypropylamino)-4-methyl-1-nitroacridine | 2 | 233 |
| 9-(2'-acetoxyethylamino)-4-methyl-1-nitroacridine | 8 | 233 |
| 9-(2'-propionoxyethylamino)-4-methyl-1-nitroacridine | 8 | 214 |
| 9-(3'-acetoxypropylamino)-4-methyl-1-nitroacridine | 8 | 157 |
| 9-(2'-propionoxypropylamino)-4-methyl-1-nitroacridine | 8 | 257 |
| 9-(2'-hydroxyethylamino)-4-methoxy-1-nitroacridine | 16 | 200 |
| 9-(3'-hydroxypropylamino)-4-methoxy-1-nitroacridine | 2 | 157 |
| 9-(4'-hydroxybutylamino)-4-methoxy-1-nitroacridine | 32 | 200 |
| 9-(4'-hydroxybutylamino)-7-methoxy-1-nitroacridine | 2 | 157 |
| 9-(2'-acetoxyethylamino)-7-methoxy-4-methyl-1-nitroacridine | 25 | 133 |
| 9-(3'-hydroxypropylamino)-7-methoxy-4-methyl-1-nitroacridine | 16 | 183 |
| 9-(4'-hydroxypropylamino)-7-methoxy-4-methyl-1-nitroacridine | 8 | 183 |
| 9-(3'-acetoxypropylamino)-7-methoxy-4-methyl-1-nitroacridine | 16 | 217 |
| 9-(2'-butyloxyethylamino)-4-methyl-1-nitroacridine | 8 | 217 |

Antitumor Activity of 9-(2'-hydroxyethylamino)-4-methyl-1-nitroacridine in Dunning G Induced Tumors in Copenhagen Rats Four to five week old Copenhagen rats are purchased from Harlan Sprague Dawley, Indianapolis, Ind., and allowed to acclimate for one week, feeding on Purina 5001 rat chow. At the end of one week, the rats are randomized into different experimental groups. Body weights of the animals measured twice a week.

Live Dunning G cells (one million/rat) are injected subcutaneously in all animals to induce tumors. Dunning G cells are non-metastatic tumor producing prostate cancer cells derived from spontaneous tumors from Copenhagen rats. Dunning G and MAT-LyLu cells (Yedavelli et al, 1999, Int. J. Mol. Med. 4:243–248) are grown in RPMI 1640 containing 10% fetal bovine serum (FBS) supplemented with penicillin (50 IU/mL), streptomycin (50 μg/mL), 2 mM L-glutamine and 2.5 mM dexamethasone. Cells are fed twice a week and are trypsinized with 0.05% trypsin-EDTA at 70–80 percent cell confluency.

Animals are injected i.p twice a week with 9-(2'-hydroxyethylamino)-4-methyl-1-nitroacridine (0.8 or 1.0 mg/Kg body weight) 1-nitro-9-hydroxyethylaminoacridine (0.6 mg/Kg body weight) twice a week for three weeks. Injections are started on day 25 for animals injected with Dunning G cells when tumors are palpable (0.5 cm). All animals are housed in hanging cages with three/four animals per cage and had ad libitum access to food and drinking water and are kept on twelve hour diurnal cycle. All injections and tumor measurements are performed under light anesthesia (metofane inhalation). Experimental end point measurements include body weight, tumor incidence. The experiment is terminated when the tumor size in the control animals is 3 cms diameter. Sacrifice of the animals is done by carbon dioxide asphyxiation.

Stock solution of 9-(2'-hydroxyethylamino)-4-methyl-1-nitroacridine is made in dimethylsulfoxide at 0.16 mg/ml. All drugs for injection in animals are diluted in PBS such that the total volume injected is between 0.1 to 0.2 mL. Stock solution of 1-nitro-9-hydroxyethylaminoacridine is made in dimethylsulfoxide at 0.12 mg/ml.

The results obtained are shown in FIG. 1. It appears that tumor reduction is evident two weeks after treatment withdrawal. Treatment 1-nitro-9-hydroxyethylaminoacridine results in a 50% reduction of tumors; treatment with 0.8 mg/kg of 9-(2'-hydroxyethylamino)-4-methyl-1-nitroacridine results in a 65% reduction of tumors and treatment with 1.0 mg/kg of 9-(2'-hydroxyethylamino)-4-methyl-1-nitroacridine results in a 75% reduction of tumors.

Antitumor Activity of 9-(2'-hydroxyethylamino)-4-methyl-1-nitroacridine on Tumors in Nude Mice Tumors are induced in six week old Balb c/nu/nu mice which are allowed to acclimate for two weeks by subcutaneous injection of $2 \times 10^6$ TSU cells per mouse. TSU cells are human prostate cancer cells (Iizumi et al., 1987, J. Urol. 137:1304–1306). TSU cells are grown in RPMI-1640 medium supplemented with 10% fetal bovine serum and the antibiotics penicillin (50 IU/ml), streptomycin (50 μg/ml) and 2 mM L-glutamine. Cells are fed with fresh media twice a week and are trypsinized using 0.05% trypsin-EDTA. Cells used for injection are always in the log phase of their growth (70–80%) confluent flask and cell viability is checked by trypan-blue exclusion test prior to injection. Only cells >95% confluent are used.

Figure 2:
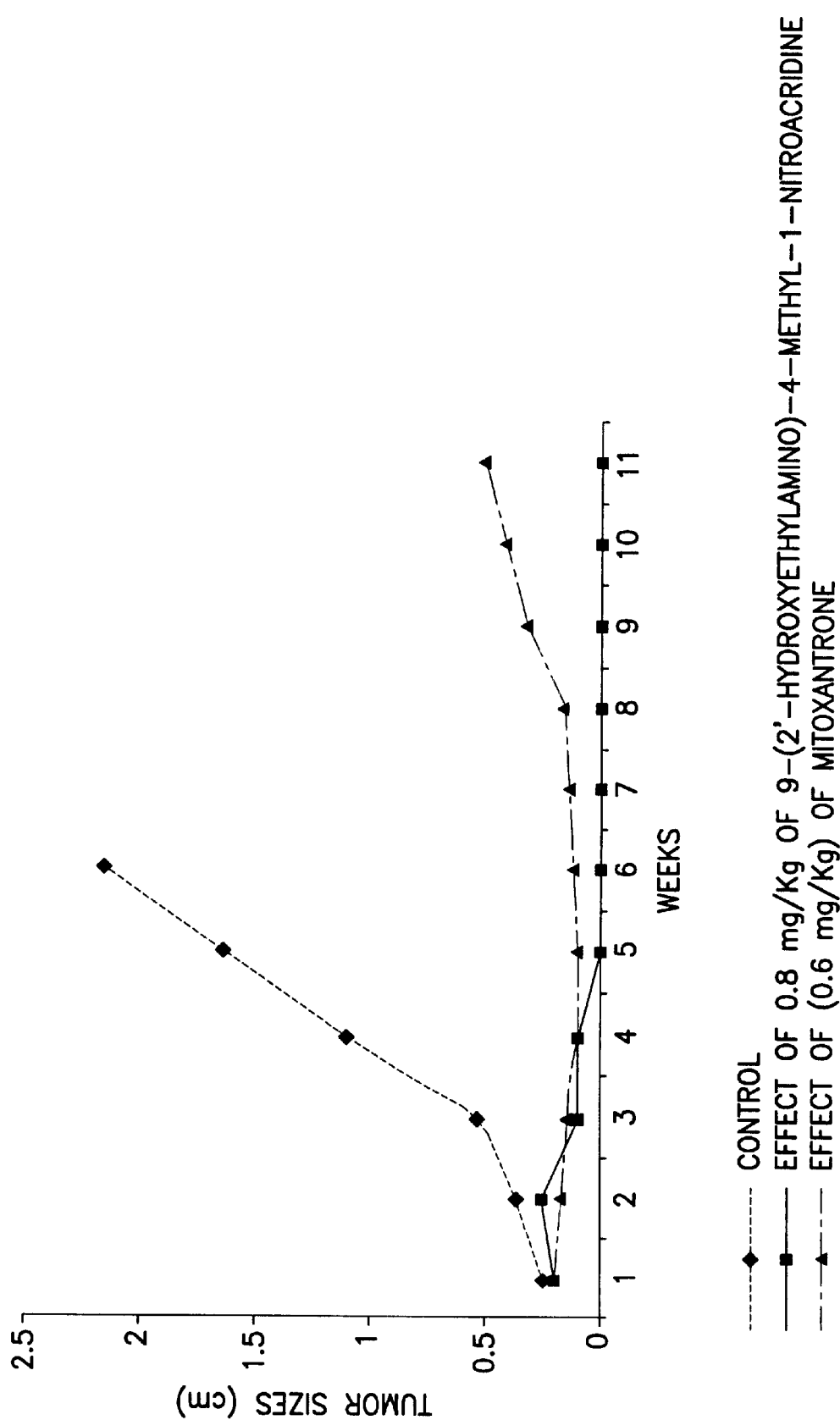
FIG. 2 shows the effect of 9-(2'-hydroxyethylamino)-4-methyl-1-nitroacridine on reducing human prostate tumor xenografts in nude mice. ------♦------ Shows control, ━━━■━━━ shows the effect of 0.8 mg/Kg of 9-(2'-hydroxyethylamino)-4-methyl-1-nitroacridine ━ ─▲─ ─ shows the effect of (0.6 mg/Kg) of mitoxantrone.

Tumors are palpable in the mice by day 7 when treatment with the two drugs, mitoxantrone (0.6 mg/kg) and 9-(2'- hydroxyethylamino)-4-methyl-1-nitroacridine (0.8 mg/kg) is initiated. Treatment is continued twice weekly for three weeks. Mice are lightly anesthetized and tumors are measured and are weighed weekly. The stock concentrations of the drug are 0.12 mg/ml in PBS for mitoxantrone and 0.16 mg/ml in dimethylsulfoxide (DMSO) for 9-(2'-hydroxyethylamino)-4-methyl-1-nitroacridine. Mice are housed 5 animals/cage. As is evident for FIG. 2, treatment for three weeks with 9-(2'-hydroxyethylamino)-4-methyl-1-nitroacridine brought about a reduction of the tumors until completely tumor free by five weeks and remained in force until 11 weeks, the maximum observation period. During this period, the group treated with mitoxantrone showed a reduction till three weeks and the tumors started growing eight weeks after withdrawal of therapy.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A 1-nitro-9-alkylaminoacridine compound having the structure I

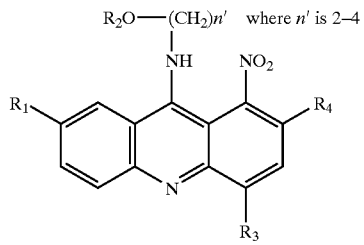

wherein when $R_1$ is H, $R_2$ is $CO(CH_2)_nCH_3$ or H, where n=1–8, $R_3$ is $(CH_2)_nCH_3$, where n=0–1 or $O(CH_2)_nCH_3$, where n=0–1 and $R_4$ is H, $(CH_2)_nCH_3$, or $O(CH_2)_nCH_3$, where n=0–1;

wherein when $R_1$ is $O(CH_2)_nCH_3$, where n=0–1, and $R_2$ is H, $R_3$ and $R_4$ is H and wherein when $R_1$ is $O(CH_2)_nCH_3$, where n=0–1 and $R_2$ is $CO(CH_2)_nCH_3$, where n=1–8 $R_3$ is H, $(CH_2)_nCH_3$, where n=0–1 or $O(CH_2)_nCH_3$, where n=0–1, and $R_4$ is H, $(CH_2)_nCH_3$, or $O(CH_2)_nCH_3$, where n=0–1 or salt thereof.

2. The compound according to claim 1, wherein the compound is selected from the group consisting of 9-(2'-hydroxyethylamino)-4-methyl-1-nitroacridine, 9-(2'-hydroxyethylamino)-7-methoxy-1-nitroacridine, 9-(2'-hydroxyethylamino)-7-methoxy-4-methyl-1-nitroacridine, 9-(3'-hydroxypropylamino)-7-methoxy-1-nitroacridine, 9-(3'-hydroxypropylamino)-4-methyl-1-nitroacridine, 9-(2'-acetoxyethylamino)-4-methyl-1-nitroacridine, 9-(2'-propionoxyethylaznino)-4-methyl-1-nitroacridine, 9-(3'-acetoxypropylamino)-4-methyl-1-nitroacridine, 9-(2'-propionoxypropylamino)-4-methyl-1-nitroacridine, 9-(2'-hydroxyethylamino)-4-methoxy-1-nitroacridine, 9-(3'-hydroxypropylamino)-4-methoxy-1-nitroacridine, 9-(4'-hydroxybutylamino)-4-methoxy-1-nitroacridine, 9-(4'-hydroxybutylamino)-7-methoxy-1-nitroacridine, 9-(2'-acetoxyethylamino)-7-methoxy-4-methyl-1-nitroacridine, 9-(3'-hydroxypropylamino)-7-methoxy-4-methyl-1-nitroacridine, 9-(4'-hydroxypropylamino)-7-methoxy-4-methyl-1-nitroacridine, 9-(3'-acetoxypropylamino)-7-methoxy-4-methyl-1-nitroacridine, and 9-(2'-butyloxyethylamino)-4-methyl-1-nitroacridine.

3. A composition comprising the compound of claim 1 or pharmaceutically acceptable salt thereof and a pharmaceutically acceptable carrier.

4. A method for inhibiting tumor growth in a mammal in need thereof, wherein said tumor is selected from the group consisting of adenocarcinoma, colon tumor, prostate tumor and sarcoma, in a mammal comprising administering to said mammal an amount of the 1-nitro-9-alkylaminoacridine compound of claim 1 effective to inhibit said tumor growth.

5. The method according to claim 4, in which the mammal is a human patient.

6. A method for inhibiting prostate tumor growth in a human patient in need thereof, comprising administering to said patient an amount of the 1-nitro-9-alkylaminoacridine compound of claim 1 effective to inhibit said tumor growth.

7. A method for inhibiting tumor growth in a mammal in need thereof, wherein said tumor is selected from the group consisting of adenocarcinoma, colon tumor, prostate tumor and sarcoma, comprising administering to said mammal an amount of the composition of claim 3 effective to inhibit tumor growth.

8. The method according to claim 7, wherein the mammal is a human patient.

9. A method for inhibiting prostate tumor growth in a human patient in need thereof, comprising administering to said patient an amount of the composition of claim 3 effective to inhibit said tumor growth.

10. A method for inhibiting metastases of a tumor in a mammal in need thereof, wherein said tumor is selected from the group consisting of adenocarcinoma, colon tumor, prostate tumor and sarcoma, comprising administering to said mammal an amount of the 1-nitro-9-alkylaminoacridine derivative of claim 1 effective to inhibit metastases of said tumor.

11. The method according to claim 10, wherein said mammal is a human patient.

12. A method for inhibiting metastases of a tumor in a mammal in need thereof, wherein said tumor is selected from the group consisting of adenocarcinoma, colon tumor, prostate tumor and sarcoma, comprising administering to said mammal an amount of the composition of claim 3 effective to inhibit metasases of said tumor.

13. The method according to claim 12, wherein said mammal is a human patient.

14. A method for inhibiting metastases of a prostate tumor in a human patient in need thereof comprising administering to said patient an amount of the 1-nitro-9-alkylaminoacridine compound of claim 1 effective to inhibit metastases of said tumor.

15. A method for inhibiting metastases of a prostate tumor in a human patient in need thereof, comprising administering to said patient an amount of the composition of claim 3 effective to prevent metastases of said tumor.

16. A method for obtaining the 1-nitro-9-aminoacridine compound of claim 1 comprising (a) reacting a compound having the formula III

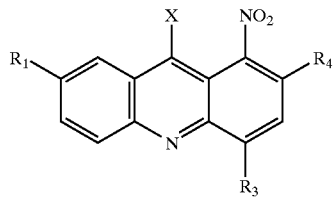

wherein when $R_1$ is H, $R_3$ is $(CH_2)_nCH_3$, where n=0–1 or $O(CH_2)_nCH_3$, where n=0–1 and $R_4$ is H, $(CH_2)_nCH_3$, or $O(CH_2)_nCH_3$, where n=0–1;

wherein when $R_1$ is $O(CH_2)_nCH_3$, where n=0–1 $R_3$ is H, $(CH_2)_nCH_3$, where n=0–1 or $O(CH_2)_nCH_3$, where n=0–1, and $R_4$ is H, $(CH_2)_nCH_3$, or $O(CH_2)_nCH_3$, where n=0–1 or salts thereof Wherein X is Cl, or phenoxy With a hydroxyalkylamino derivative and (b) isolating said 1-nitro-9-alkylaminoacridine compound.

17. The method according to claim 16 which further comprises reacting the 1-nitro-9-alkylaminoacridine compound with an acylating agent.

18. A compound having the formula III

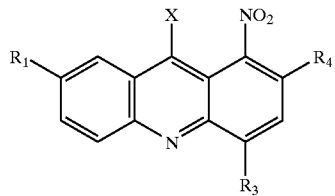

Wherein X is phenoxy, $R_1$ is H, $O(CH_2)_nCH_3$, where n=0–1, $R_3$ is $(CH_2)_nCH_3$, where n=0–1 and $R_4$ is H, $(CH_2)_nCH_3$, where n=0–1 or $O(CH_2)_nCH_3$, where n=0–1.

19. A compound having the formula III

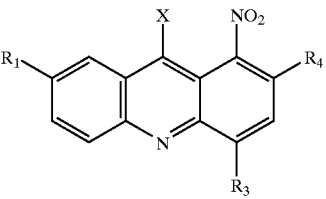

Wherein X is Cl, $R_1$ is $O(CH_2)_nCH_3$, where n=0–1, where n=0–1, $R_3$ is $(CH_2)_nCH_3$, where n=1 and $R_4$ is H, $(CH_2)_nCH_3$, where n=0–1 or $O(CH_2)_nCH_3$, where n=0–1.

20. A salt of 1-nitro-9-alkylaminoacridine compound having the structure I

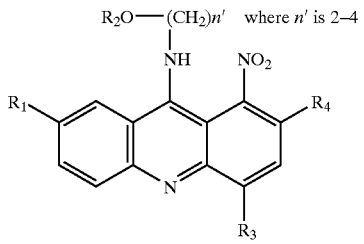

wherein when $R_1$ is H, $R_2$ is $CO(CH_2)_nCH_3$ or H, where n=1–8, $R_3$ is $(CH_2)_nCH_3$, where n=0–1 or $O(CH_2)_nCH_3$, where n=0–1 and $R_4$ is H, $(CH_2)_nCH_3$, or $O(CH_2)_nCH_3$, where n=0–1;

wherein when $R_1$ is $O(CH_2)_nCH_3$, where n=0–1, and $R_2$ is H, $R_3$ and $R_4$ is H and wherein when $R_1$ is $O(CH_2)_nCH_3$, where n=0–1 and $R_2$ is $CO(CH_2)_nCH_3$, where n=1–8, $R_3$ is H, $(CH_2)_nCH_3$, where n=0–1 or $O(CH_2)_nCH_3$, where n=0–1, and $R_4$ is H, $(CH_2)_nCH_3$, or $O(CH_2)_nCH_3$, where n=0–1.

21. The salt of claim 20, wherein said salt is selected from the group consisting of lactic, methanesulfonic acid and tartaric acid.

22. The salt of claim 20, wherein said compound is 9-(2'-hydroxyethylamino)-4-methyl-1-nitroacridine.

23. The salt of claim 20, wherein said salt is a methane sulfonic acid salt.

* * * * *